(12) United States Patent
Orsén (10) Patent No.: US 6,412,288 B1
(45) Date of Patent: Jul. 2, 2002

(54) POINT COOLING

(75) Inventor: Mikael Orsén, Åkersberga (SE)

(73) Assignee: AGA Aktiebolag, Lidingo (SE)

( * ) Notice: Subject to any disclaimer, the term of this patent is extended or adjusted under 35 U.S.C. 154(b) by 0 days.

(21) Appl. No.: 09/762,359

(22) PCT Filed: Aug. 5, 1999

(86) PCT No.: PCT/SE99/01336

§ 371 (c)(1),
(2), (4) Date: Apr. 13, 2001

(87) PCT Pub. No.: WO00/07790

PCT Pub. Date: Feb. 17, 2000

(30) Foreign Application Priority Data

Aug. 6, 1998 (SE) ................................. 9802683

(51) Int. Cl.⁷ ............................. F17C 9/02; F17C 7/02
(52) U.S. Cl. .......................................... 62/50.2; 62/52.1
(58) Field of Search ............................. 62/50.2, 52.1, 62/50.1

(56) References Cited

U.S. PATENT DOCUMENTS

| | | | | |
|---|---|---|---|---|
| 3,427,815 A | * | 2/1969 | Pitlor | 62/52.1 |
| 3,760,599 A | * | 9/1973 | Bose | 62/49.1 |
| 4,367,743 A | * | 1/1983 | Gregory | 128/303.1 |
| 4,962,891 A | * | 10/1990 | Layden | 239/597 |
| 5,154,062 A | | 10/1992 | Gaumer, Jr. et al. | |
| 5,214,925 A | * | 6/1993 | Hoy et al. | 62/50.6 |

FOREIGN PATENT DOCUMENTS

| | | |
|---|---|---|
| DE | 33 22 312 | 1/1985 |
| EP | 0 872 563 | 10/1998 |
| SE | 506 728 | 2/1998 |

* cited by examiner

*Primary Examiner*—William C. Doerrler
(74) *Attorney, Agent, or Firm*—Perne & Gordon LLP (57) ABSTRACT

The present invention relates to a method and a device for point cooling. The cooling device comprises a cooling channel provided with a defined small end surface (9, 39) and an outlet valve (11) separated therefrom, a container (13) with liquid carbon dioxide and an access conduit (15a–c, 43) connected to said container (13) provided with a nozzle (17, 45) localized to said cooling channel, whereby liquid carbon dioxide is brought to flow from the container out through said nozzle. The invention further comprises to choose the overpressure of the container, adjust the outlet valve (11) and design the nozzle in such a way that the pressure in the cooling channel (7, 35) is kept above the so-called triple point of carbon dioxide and that the distance between the nozzle (17, 45) and the defined small end surface (9, 39) is adapted so as to substantially gasify the carbon dioxide at said end surface. The device is particularly intended for point cooling of a injection moulded or cast detail (31) with a sharp edge (33) or a varying material thickness, whereby the cooling channel (35) is provided in a moulding tool (37) intended for the detail.

10 Claims, 6 Drawing Sheets

POINT COOLING

This application claims the benefit of International Application Number PCT/SE99/01336, which was published in English on Feb. 17, 2000.

TECHNICAL FIELD

The present invention relates to a method and a device for point cooling, particularly for point cooling of an accessible surface or of a detail with a sharp edge and/or a varying material thickness at injection moulding or casting.

RELATED ART

Injection moulding is a manufacturing process, wherein plastic is injected into a moulding tool under pressure and solidifies. The moulding tool is substantially a negative of the detail which is to be manufactured. Typical injection pressures vary from 5000 to 20000 psi. Since these high pressures exist, the moulding tool, which is often composed of a two part mould, has to be held clamped in a closed position during injection and cooling. This clamping force shall be considerably high.

Injection moulding may be used for manufacturing a large number of details with a very high precision. Tolerances better than 0.0025 mm are easily achieved with a suitable combination of moulding tool design, material and detail design. Furthermore, injection moulding is a high capacity process. Cycle times vary from a few seconds to several minutes depending on the size and form of the injection moulded detail.

A problem with the technique, particularly in injection moulding of details with sharp edges, varying material thickness or narrow cavities, is the occurrence of so-called hotspots. These deformations arise when part of the detail is solidifying at different speeds in different, often substantially reverse directions.

A traditional way of solving this problem is to form cooling channels to the hotspot-exposed part and into these channels insert cooling rods, i.e. rods with high thermal conductivity which are cooled. Alternatively, cooling water or a cooled concentrated gas is directed into the cooling channels. Hereby, also the cycle time may be very considerably shortened. Sometimes this cooling may, however, be unsufficient.

The German patent document DE 3 322 312 describes a cooling method in manufacturing an injection moulded detail in a moulding tool with a core. In the core there is a recess, in which a conduit for liquid gas is existing. This conduit is, via an access conduit provided with a magnetic valve, in connection with a tank containing a liquid gas, e.g. nitrogen, air, carbon dioxide or argon. Furthermore, the recess has an exhaust conduit, wherein there is a thermometer. A regulation and control unit may be used to control the magnetic valve by means of temperature measured in the reverse conduit. Cooling will be existing over a relatively large surface.

A further method using liquid carbon dioxide as cooling medium is dry precision cooling, DPC, which method is used for cooling during dry precision grinding. The method comprises that a mixture of carbon dioxide snow and gas are supplied to the tool and the workpiece in a thin, highly effective cooling jet.

However, it is desirable to find a method and a device, which effectively may cool very small surfaces of an arbitrary kind. Surfaces of particular interest in this respect are accessible open surfaces, e.g. at heat generating electronic components or at human tissue, and surfaces at details with a shart edge and/or varying material thickness at injection moulding or casting.

SUMMARY OF THE INVENTION

Thus, it is an object of the present invention to provide a method and a device for effective, fast and reliable point cooling.

A further object of the invention is to provide a method and a device, particularly for point cooling of an accessible open surface.

Another object of the invention is to provide a method and a device, particularly for point cooling of a detail with a sharp edge and/or varying material thickness at injection moulding or casting.

This and other objects are attained according to one aspect of the invention by a method for point cooling, which method comprises providing a cooling channel with a defined end surface and an outlet valve separated therefrom, a container with liquid carbon dioxide and an access conduit, provided with a nozzle, connected to said container and localized to said cooling channel. Liquid carbon dioxide is brought to flow from the container and out through said nozzle.

In this respect the overpressure of the container, the throttling of the outlet valve and the design/size of the nozzle are to be chosen so that the pressure in the channel is held over the so-called triple point pressure of carbon dioxide, i.e. 5.18 bars. Furthermore, the distance between the nozzle and the end surface shall be adapted so that mainly all carbon dioxide is gasified at the end surface. A corresponding inventive device for point cooling comprises said parts arranged in a described way.

Preferably, the pressure in the channel is held within the interval 5.18–8 bars. The most effective cooling is achieved, if the pressure in the channel is held substantially immediately above the triple point pressure.

A corresponding inventive method and device, particularly intended for point cooling of an accessible surface, particularly comprise that the cooling channel with its end surface is composed of the interior of a tubular means with an end surface of a material of a high thermal conductivity.

An inventive method and device, particularly intended for point cooling of an injection moulded or cast detail with a sharp edge or a varying material thickness particularly comprise that the cooling channel is formed in a moulding tool intended for manufacturing the detail, said end surface being localized in the vicinity of the sharp edge or the varying material thickness of the detail.

An advantage of the point cooling method and device according to the present invention is that cooling is applied very rapidly and effectively and of very small surfaces.

A further advantage of the invention is that a smooth and continuous cooling effect is achieved.

Yet a further advantage of the invention is that the cycle time for injection moulding or casting may be shortened.

Laboratory experiments have i.a. shown that it is extremely important to hold the pressure above the triple point pressure both momentarily and in long term to avoid any instabilities, such as a heavily varying pressure caused thereby that some carbon dioxide snow does not evaporate but at least partly plugs up the outlet. On the other hand, too high pressures may also result in similar instabilities. Here, all liquid is not evaporated at the end surface but some amount continues to the outlet, where it will condense to snow.

More advantages of the invention will be apparent in the following description.

SHORT DESCRIPTION OF THE DRAWINGS

The invention will be closer described below with reference to FIGS. 1–7, which are only shown to illustrate the invention and shall therefore in no way limit the same.

PREFERRED EMBODIMENTS

In the following description, for the purpose of explanation and not limitation of the invention, specific details are given, such as particular applications, techniques, etcetera, to give a thorough understanding of the invention. However, it shall be obvious to anyone skilled in the art that the invention may be practised in other forms than these.

Figure 1:
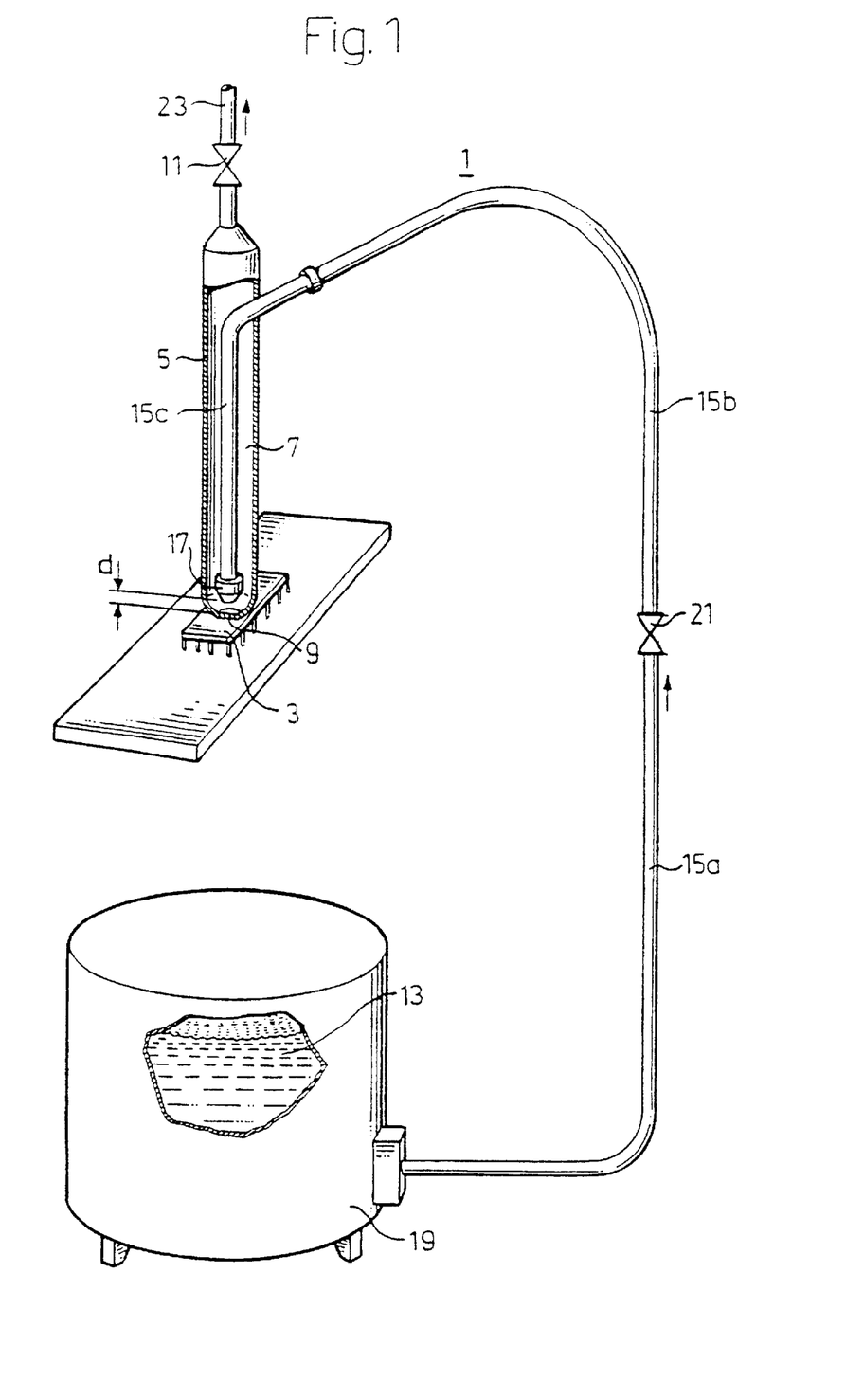
FIG. 1 shows an embodiment of the present invention, particularly intended for point cooling of an accessible surface.

In FIG. 1 is shown an inventive embodiment of a device 1 for point cooling of an accessible open surface, here in the form of an upper surface of an electronic component 3. The cooling device 1 comprises a tubular means 5, the interior of which is constituted by a cooling channel 7 provided with an end surface 9 in one of its ends. The tubular means 5, particularly its end surface, shall be of a material of high thermal conductivity in order to effectively transport cold through the end surface. The cooling channel 7 has further an outlet valve 11 separated from the end surface, preferably located in the other end of the channel. Furthermore, there is comprised a container 13 with liquid carbon dioxide 19 and an access conduit 15a, 15b, 15c provided with a nozzle 17 localized in said cooling channel 7, particulary in the vicinity of the first end of the cooling channel.

Liquid carbon dioxide 19 is brought to flow from the container 13 out through said nozzle 17. In this respect the overpressure of the container 13, the throttling of the outlet valve 11 and design/size of the nozzle 17 shall be chosen in order to hold the pressure in the cooling channel 15 during cooling always above the so-called triple point pressure of carbon dioxide, i.e. 5.18 bars. Preferably, the pressure in the channel is held within the interval 5.18–8 bars. The most effective cooling is achieved, if the pressure in the channel is held substantially immediately above the triple point pressure, which is described closer below. Furthermore, the distance d between the nozzle 17 and the end surface 9 shall be so designed that mainly all carbon dioxide is gasified at the end surface 9.

The tubular means 5 is preferably rounded at its lower part in order to achieve the desired local cooling. The means may alternatively have a pointed, a dull or a bevelled form (not shown in the figures). Furthermore, the access conduit 15a, 15b, 15c may be provided with a valve 21 for adjustment of the desired flow/pressure. Preferably, the access conduit is comprised of three different parts; a fixed tubular part 15a, which connects to the container 13, a fixed tubular part 15c positioned in the cooling channel 7 and to which the nozzle 17 is connected and an intermediate conduit 15b, which may be easily bendable or may be in a somewhat stiffer design. In the former case the conduit 15b may preferably comprise, or be constituted by, a plastic hose. Hereby the cooling part of the cooling device, i.e. the tubular means 5 with the cooling channel 7 and the end surface 9 as well as the tubular part 15c with the nozzle 17, become movable. Preferably, the cooling part has the size of a pen or somewhat bigger; in this respect the term "cooling pen" may thus be suitable.

The outlet valve 11, which is connected to the other end of the cooling channel 7, is further connected to an exhaust conduit 23, which may be short, as shown in FIG. 1, or longer and e.g. parallel with the access conduit 15a, 15b, 15c.

Figure 2:
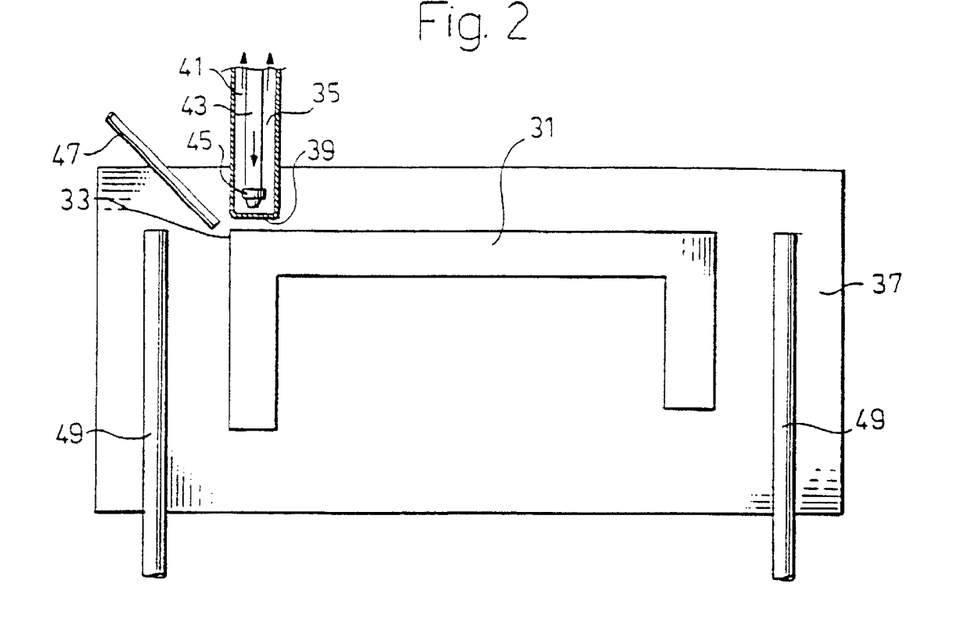
FIG. 2 shows an inventive embodiment, particularly intended for point cooling of a detail with a sharp edge and/or a varying material thickness during manufacture using injection moulding or casting.

Part of an inventive device especially intended for point cooling of an injection moulded or cast detail 31 with a sharp edge 33 or varying material thickness is shown in FIG. 2 (note that some parts, such as the container with liquid carbon dioxide, the outlet valve and the exhaust conduit, are not shown in FIG. 2). The device preferably comprises forming at least part of a cooling channel 35 in a moulding tool 37 intended for the detail 31 with an end surface 39 localized in the vicinity of the sharp edge 33 or the varying material thickness of the detail. An outlet valve (not shown) connects to the upper part 41 of the cooling channel. An access conduit 43 is connected between a container containing liquid carbon dioxide (not shown) and a nozzle 45 localized to the cooling channel 35, particularly to the vicinity of its end surface 39.

Just like in the embodiment described above the liquid carbon dioxide is arranged to flow from the container through the access conduit and out through said nozzle to be evaporated mainly at the end surface 39 of the cooling channel. Gasified carbon dioxide flows further up in the cooling channel and through the outlet valve. According to the idea of the invention the overpressure of the container, the throttling of the outlet valve and the design/size of the nozzle 39 shall be chosen so that the pressure in the cooling channel 35 during cooling always is above the so-called triple point pressure for carbon dioxide, i.e. 5.18 bars. Preferably, the pressure in the channel is held within the interval 5.18–8 bars, particularly just above the triple point pressure.

Furthermore, a thermoelement may be applied in a channel 47 in the moulding tool 37 for temperature measurement. Furthermore, or alternatively, a pressure sensor may be applied in the cooling channel (not shown) for measurement of the pressure in said channel. These measurements may be performed during installation and initial adjustment of the inventive device and/or at regular intervals. The measurement data may also constitute data input to an automatic regulation system for regulation of the above-mentioned parameters in order to achieve an optimal function.

Figure 3:
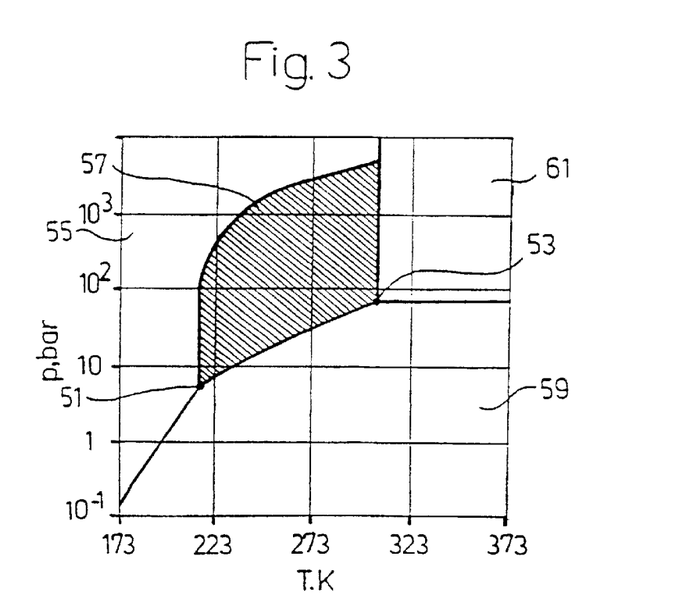
FIG. 3 shows a pressure-temperature-(pT-) diagram of carbon dioxide.

For the continued discussion it is suitable to know how the pressure and the temperature affect the carbon dioxide. FIG.

3 shows accordingly a phase diagram (pT-diagram) of carbon dioxide with the triple point 51 at p=5.18 bars and T=−56.6° C. and the critical point 53 at p=73.8 bars och T=31° C. indicated. The phases of carbon dioxide are indicated with the reference numerals 55 for solid, 57 for liquid and 59 for gaseous phases. 61 is indicating overcritical carbon dioxide.

It has thus been established that maximal cooling effect is achieved at a pressure just above the triple point pressure. From this pressure and up to a bar somewhat higher we have an optical cooling effect. At higher pressures the cooling effect decreases or, as it may also be expressed, the heat exchange capacity decreases. Theoretically the function may be described in the following manner.

p<5.18 bars: only snow (solid carbon dioxide) and gas exist in the cooling channel. The snow is evaporated only partly at the end surface in the cooling channel and thus some part of the snow is blown out towards the outlet valve and plugs the outlet. The result will be instabilities, which may be seen in the pressure, which fluctuates heavily (see further FIGS. 4–6 and the discussions in connection with these figures). A slight advantage is in itself that as the pressure, due to partial clogging of the outlet, raises above 5.18 bars, a very large increase of the cooling effect may momentaneously be obtained.

5.18<p<7–8 bars: The region of optimal cooling effect and at which pressure the cooling channel shall be held according to the present invention. Thanks to the pressure in the container carbon dioxide is entering in liquid form and hits the end surface and the cooling capacity is maximal relatively close to the triple point pressure. Furthermore, no snow is created at the outlet; only gas is flowing out. The conclusion is that all available evaporation heat is used at the desired position, i.e. at the end surface. It may also be so that an improbably effective, extraordinary evaporation is achieved dependent on the fact that all three phases probably coexist.

p>7–8 bars: When the pressure rises, it is seen that large amounts of snow in the outlet are created, i.e. cooling is taken place at the wrong position. This may be understood as the liquid has only been heated at the end surface and that the true evaporation is taken place in the outlet. This effect appears at a pressure of one to a few bars above the triple point pressure. The effect will be heavier the higher the pressure is. This is also seen on the cooling effect which is decreased.

The ideal would of course lie precisely above 5.18 bars but one must have such a marginal that the pressure never falls below 5.18 bars, since here a severe decrease of the cooling effect occurs. When the decrease of the cooling effect is less severe upwards in pressure, a security margine of one or a few bars in this direction ought to be ensured.

When a liquid gas hits a surface and evaporates during classical cryotechnical point cooling, it may, for cooling using nitrogen, exist large isolation problems. When carbon dioxide is utilized, a container of 50–60 bars pressure is used, dependent on its temperature, and when equilibrium prevails, these isolations problems are not there and, if they are, they are so at least to a much smaller extent.

With liquid nitrogen the same order of cooling effect may be achieved but some limitation of the outlet may not be achieved. At a guess, approximately 80–90% of the injected nitrogen does not have time to be evaporated at the small end surface. This "nitrogen surplus" is again flowing out and makes the technique unusable. If cooling is to be performed by use of liquid nitrogen, the evaporation surface has to be considerably increased, as e.g. is the case when using a core.

The point cooling technique according to the present invention is intended for very small surfaces, principally to be considered as points. Dimensions which, in this respect, may be mentioned and which are of particular interest are "point diameters" of approximately 3–5 mm, but also larger surfaces of about 5–8 mm are of interest. However, the present invention looses in exclusivity the larger surfaces that are cooled.

Thanks to the high heat transfer described above that is possible to achieve with carbon dioxide and pressure control/regulation in the cooling channel, cooling of such a small surface may be performed. This is not possible when using nitrogen, where one has to work with classical evaporation, i.e. boiling of a liquid.

FIGS. 4–7 are diagrams of the time development of pressure and temperature during point cooling using a particular embodiment of the present invention developed for the laboratory. In this respect the different parameters of interest, i.e. nozzle diameter, outlet design and distance between nozzle and end surface, could be varied one at a time. In all diagrams the triple point pressure and temperature are indicated.

The embodiment comprises a vertical cooling channel, approximately 60 mm deep and 7 mm in diameter, in a metal block, which channel terminates downwards with the end surface, which is to be cooled. The access conduit has an outer diameter of 5 mm and an inner diameter of 1 mm. The container containing liquid nitrogen connected to the access conduit is comprised of a bottle with a dip tube, in which carbon dioxide of an overpressure of about 60 bars is kept. The end surface of the cooling channel is spark-machined, which ought to give a larger effective surface and thus a better heat transfer. The temperature was measured at a point in the metal block about 5 mm below the end surface. The pressure was measured via a channel of a diameter of 3 mm located at the cooling channel horizontally, close to the end surface. At a distance from the cooling channel and the end surface the block was kept at about 60 degrees Celsius by means of heated and thermostat-regulated water in channels. Nozzle diameter, outlet design and distance between nozzle and end surface were varied according to what will be described below.

Figure 4:
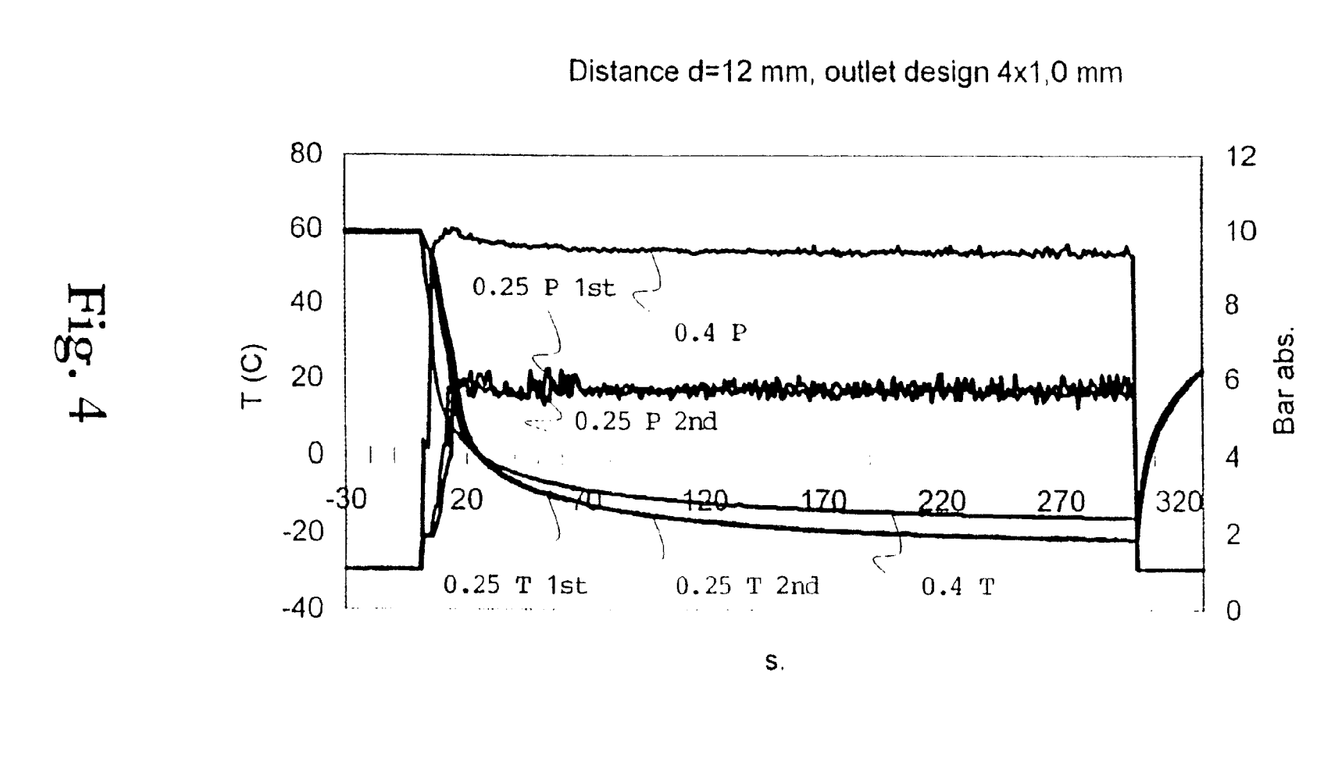
FIG. 4 shows a diagram of the pressure and temperature as a function of time for nozzles with different diameters Φ (0.25–0.4 mm) during point cooling by a particular embodiment of the present invention.

Thus, FIG. 4 shows pressure and temperature as a function of time for different nozzles with different diameters Φ (0.25–0.4). T is the temperature and P is the pressure. The distance d between nozzle and end surface is 12 mm and the outlet consists of four 1 mm wide and 0.5 mm deep grooves. The repeatability is, as can be seen, very good (see the results from two identical trials with Φ=0.25). With the parameters chosen in this way the pressure varies between 5.5 bars and up to about 9 bars. The lowest and also the most optical pressure was achieved with the smallest nozzle diameter 0.25 mm. This may be seen, as a "steady-state" temperature also is lowest in this case indicating that we have the strongest cooling effect, even if we also in the rest of the cases for some applications have an appropriate cooling effect. The problems of too high pressures seem to be that not all liquid is evaporated at the end surface, but a certain amount follows to the outlet, where it will condense to snow. In this respect the deteriorated cooling capacity may be explained.

Figure 5:
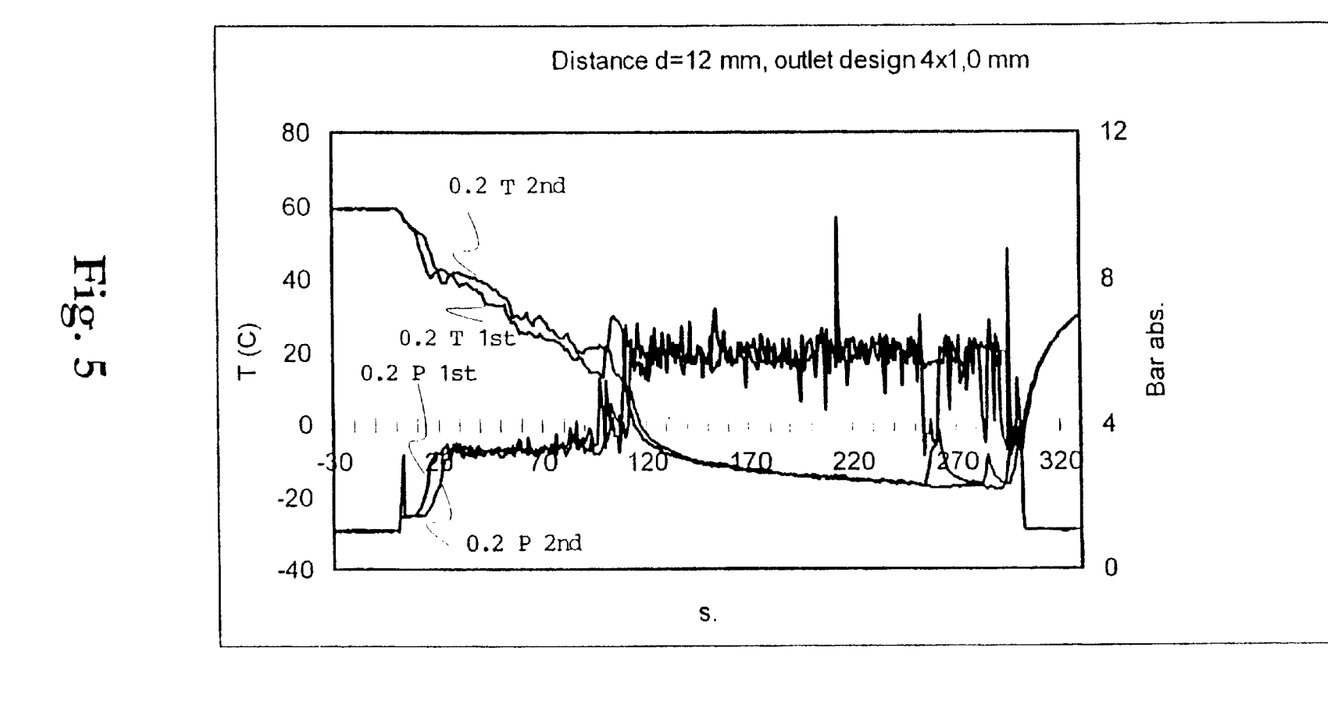
FIG. 5 shows a diagram of the pressure and temperature as a function of time for a nozzle with a diameter Φ=0.2 mm during point cooling by a particular embodiment of the present invention.

However, if we further decrease the nozzle diameter, heavy instabilities, such as heavily varying pressures, are achieved, when the triple point pressure is reached. Such phenomena may be seen in FIG. 5, where pressure and temperature as a function of time are shown for two identical trials with a nozzle of a diameter of Φ=0.2 mm. Here it may be seen that the repeatability also in this case is fairly good. The instabilities are caused thereof that a certain amount of carbon dioxide snow does not evaporate but at least partly clogs the outlet. Then the pressure increases momentarily, which will directly lead to an increased cooling effect. This is seen in the diagram at a time of 110–120 seconds. The cooling is working effectively until a time of 260–300 seconds. Then new instabilities will commence in the form of pressure reductions, which irrevocably will lead to a heavily deteriorated cooling effect. The conclusion is that a parameter choice according to the trial, the result of which is shown in FIG. 5, gives poor cooling.

Figure 6:
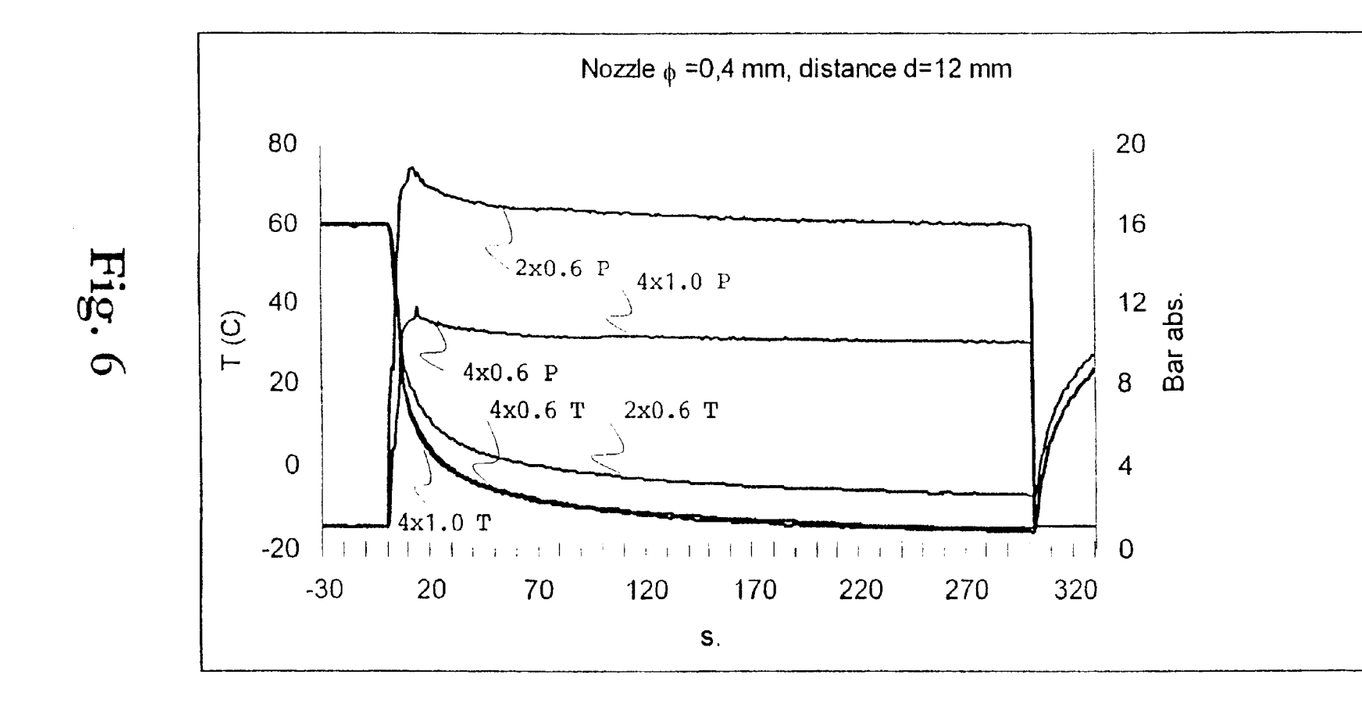
FIG. 6 shows a diagram of the pressure and temperature as a function of time for different outlet designs during point cooling by a particular embodiment of the present invention.

Furthermore, FIG. 6 shows in a diagram pressure and temperature as a function of time for different outlet designs during point cooling. The nozzle diameter and the d-distance are kept constant, 0.4 and 12 mm, respectively. Results are shown for outlet designs with two 0.6 mm wide grooves (2×0.6), with four 0.6 mm wide grooves (4×0.6) and with four 1.0 mm wide grooves (4×1.0), respectively. All grooves are 0.5 mm deep. Here, the results of trials, which have given relatively high pressure in the cooling channel (about 9–16 bars), are shown. The correlation between pressure and cooling effect is evident and at such high pressures as 16 bars a high equilibrium temperature relatively the lower pressures is obtained, i.e. poor cooling effect.

It is even possible with the naked eye to see that condensed snow is flushing out from the outlet.

Figure 7:
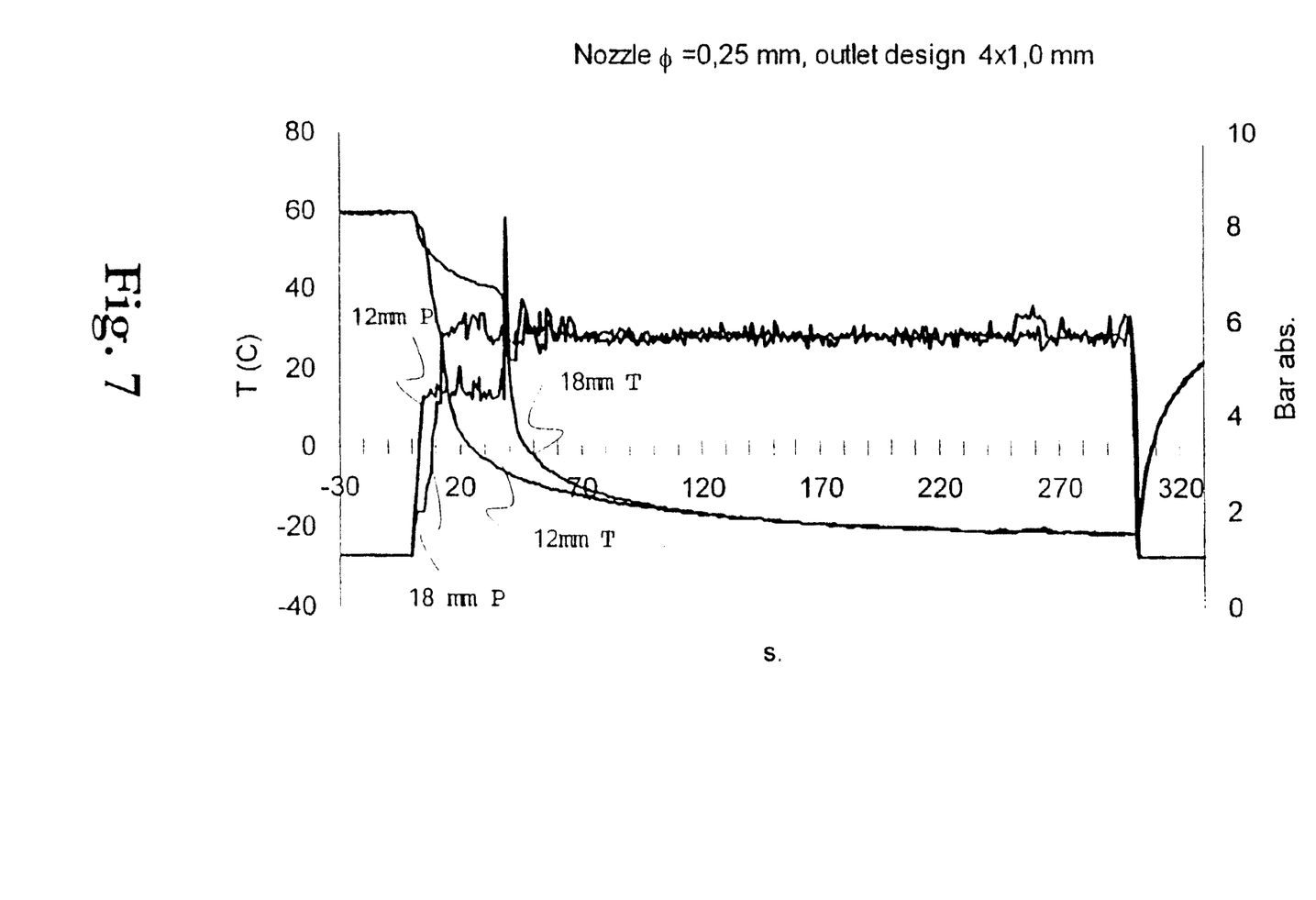
FIG. 7 shows a diagram of the pressure and temperature as a function of time for different distances d between nozzle and end surface during point cooling by a particular embodiment of the present invention.

Finally, FIG. 7 shows in a diagram pressure and temperature as a function of time for different distances d between nozzle and end surface. The nozzle diameter and the outlet design are kept constant, 0.25 mm and four 1.0 mm wide and 0.5 mm deep outlet grooves, respectively. Results are shown for distances d=12, 18 and 24 mm, respectively. Here it is seen that a fairly good cooling effect is achieved for both d=12 and 18 mm, which cooling effect further is very similar for the two cases. For d=24 mm a completely different result is, however, achieved. The distance between the nozzle and the end surface is so large that the jet of liquid carbon dioxide looses speed, is broadened and does not completey "reach" the end surface, which will give a poor evaporation and thus a poor heat transfer. The poor evaporation makes the pressure in the cooling channel not rising over the triple point pressure but lies fairly constant at about 4 bars. The cooling effect will then be extremely poor—the temperature does not even decrease beyond 30 degrees. However, it is not possible to distinguish the same type of instabilities as was the case using a small nozzle (FIG. 5).

From FIGS. 4–7 and other results the conclusion is thus drawn that suitable choices of the parameters for said embodiment are as follows: nozzle diameter Φ=0.25 mm, four 1.0 mm deep and 0.5 mm deep outlet grooves and the distance between nozzle and end surface d=12–18 mm. For other embodiments and sizes of the end surface, other parameter choices may, of course, be applied.

Experiments have shown that a cooling effect in the order of $10^2$ watts may be attained with the point cooling according to the present invention. This may be compared with traditional cooling rods, which only cool a few watts.

Except of the above-described advantages of the point cooling according to the present invention they may also include a relatively low carbon dioxide consumption for a given cooling effect, particularly relative to gases, such as e.g. nitrogen, with a considerably lower heat transfer coefficient α.

The present invention as herein described solves the problems, which are associated with the known art. It is naturally not limited to the embodiments described above and shown in the drawings, but may be modified within the scope of the appended claims.

What is claimed is:

1. A method for point cooling comprising providing a cooling channel (7, 35) having a defined small end surface (9, 39) and an outlet valve (11) separated therefrom, a container (13) containing liquid carbon dioxide (19) and an access conduit (15a, 15b, 15c, 43) connected to said container (13) provided with a nozzle (17, 45) localized to said cooling channel, and-bringing liquid carbon dioxide to flow from the container out through said nozzle, characterized by choosing the overpressure of the container (13), adjusting the outlet valve (11) and designing the nozzle (17, 45) in such a way that the pressure in the cooling channel (7, 35) is kept above the so-called triple point pressure of carbon dioxide and choosing the distance (d) between the nozzle (17, 45) and the defined small end surface (9, 39) in such a way that the carbon dioxide is substantially gasified at said end surface (9, 39).

2. The method according to claim 1, characterized by keeping the pressure in the cooling channel (7, 35) within the interval 5.18 to about 8 bars.

3. The method according to claim 1, characterized by keeping the pressure in the cooling channel (7, 35) substantially immediately above the triple point pressure.

4. The method according to any of claims 1–3, particularly intended for point cooling of an accessible surface, characterized by choosing the cooling channel (7) having the defined small end surface (9) to be comprised of the interior of a tubular means (5) having the defined small end surface (9) of a material of high thermal conductivity.

5. The method according to any of claims 1–3, particularly intended for point cooling of an injection moulded or cast detail (31) with a sharp edge (33) or a varying material thickness, characterized by providing the cooling channel (35) having the defined small end surface (39) in a moulding tool (37) intended for the detail (31), the defined small end surface (39) being located in the vicinity of the sharp edge (33) or the varying material thickness of the detail.

6. A device for point cooling comprising a cooling channel (7, 35) provided with a defined small end surface (9, 39) and an outlet valve (11) separated therefrom, a container (13) containing liquid carbon dioxide (19) and an access conduit (15a, 15b, 15c, 43) connected to said container (13) having a nozzle (17, 45) localized to said cooling channel (7, 35), the device being arranged in such a way that liquid carbon dioxide is brought to flow from the container out through said nozzle, characterized in that the overpressure of the container (13) is chosen, the outlet valve (11) is adjusted and the nozzle (17, 45) is designed in such a way that the pressure in the cooling channel (7, 35) is kept above the so-called triple point of carbon dioxide and that the distance (d) between the nozzle (17, 45) and the defined small end surface (9, 39) is such that the carbon dioxide is substantially gasified at said end surface (9, 39).

7. The device according to claim 6, characterized in that it is arranged in such a way that the pressure in the cooling channel (7, 35) is kept within the interval 5.18 to 8 bars.

8. The device according to claim 6, characterized in that it is arranged in such a way that the pressure in the cooling channel (7, 35) is kept substantially immediately above the triple point pressure.

9. The device according to any of claims 6–8, particularly intended for point cooling of an accessible surface, characterized in that the cooling channel (7) provided with the defined small end surface (9) is comprised of the interior of a tubular means (5) with the defined small end surface (9) of a material with high thermal conductivity.

10. The device according to any of claims 6–8, particularly intended for point cooling of an injection moulded or cast detail (31) with a sharp edge (33) or a varying material thickness, characterized in that the cooling channel (35) provided with the defined small end surface (39) is provided in a moulding tool (37) intended for the detail (31), the defined small end surface (39) being localized in the vicinity of the sharp edge (33) or the varying material thickness of the detail.

* * * * *